United States Patent
Peng

(10) Patent No.: US 10,912,749 B2
(45) Date of Patent: *Feb. 9, 2021

(54) CONJUGATE ACID SALT OF N,N-DIMETHYLGLYCINE WITH ORGANIC ACID, AND COMPOSITION AND USE THEREOF

(71) Applicant: GUANGZHOU INSIGHTER BIOTECHNOLOGY CO., LTD., Guangdong (CN)

(72) Inventor: Xianfeng Peng, Guangzhou (CN)

(73) Assignee: GUANGZHOU INSIGHTER BIOTECHNOLOGY CO., LTD., Guangdong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/755,152

(22) PCT Filed: Nov. 2, 2017

(86) PCT No.: PCT/CN2017/109143
§ 371 (c)(1),
(2) Date: Apr. 9, 2020

(87) PCT Pub. No.: WO2019/080155
PCT Pub. Date: May 2, 2019

(65) Prior Publication Data
US 2020/0297675 A1 Sep. 24, 2020

(30) Foreign Application Priority Data
Oct. 25, 2017 (CN) .......................... 2017 1 1010206

(51) Int. Cl.
| | | |
|---|---|---|
| *A61K 31/197* | (2006.01) | |
| *A23K 20/142* | (2016.01) | |
| *A23K 20/22* | (2016.01) | |
| *A23K 20/24* | (2016.01) | |
| *A23K 20/20* | (2016.01) | |
| *A23K 50/30* | (2016.01) | |
| *A23K 50/75* | (2016.01) | |
| *A23K 50/80* | (2016.01) | |
| *A23K 20/105* | (2016.01) | |
| *A23K 20/111* | (2016.01) | |
| *A61K 47/54* | (2017.01) | |
| *A61K 33/06* | (2006.01) | |
| *A61K 33/24* | (2019.01) | |
| *A61K 33/26* | (2006.01) | |
| *A61K 33/30* | (2006.01) | |
| *A61K 33/32* | (2006.01) | |
| *A61K 33/34* | (2006.01) | |

(52) U.S. Cl.
CPC .......... *A61K 31/197* (2013.01); *A23K 20/111* (2016.05); *A23K 20/142* (2016.05); *A23K 20/22* (2016.05); *A23K 20/24* (2016.05); *A23K 20/30* (2016.05); *A23K 50/75* (2016.05); *A23K 50/80* (2016.05); *A61K 33/06* (2013.01); *A61K 33/24* (2013.01); *A61K 33/26* (2013.01); *A61K 33/30* (2013.01); *A61K 33/32* (2013.01); *A61K 33/34* (2013.01); *A61K 47/542* (2017.08)

(58) Field of Classification Search
None
See application file for complete search history.

(56) References Cited

U.S. PATENT DOCUMENTS

| | | |
|---|---|---|
| 6,197,815 B1 | 3/2001 | Hsu |
| 8,523,975 B2 | 9/2013 | Ettlin et al. |
| 2009/0281183 A1 | 11/2009 | Yuan et al. |
| 2010/0183580 A1 | 7/2010 | Kalmar et al. |

FOREIGN PATENT DOCUMENTS

| | | |
|---|---|---|
| CN | 1091430 A1 | 8/1994 |
| CN | 1887887 A1 | 1/2007 |
| CN | 102911067 A1 | 2/2013 |
| CN | 105777534 A1 | 7/2016 |
| CN | 105884637 A1 | 8/2016 |

*Primary Examiner* — Brian J Davis
(74) *Attorney, Agent, or Firm* — Kam Wah Law

(57) ABSTRACT

The present invention relates to a conjugate salt of N,N-dimethylglycine with metal and organic acid, and a preparation method and use thereof. The conjugate salt of N,N-dimethylglycine with metal and organic acid has a following structural formula: $[(CH_3)_2NCH_2COO]_n.M.[Organic\ acid]$, wherein, n is 1 or 2; M is selected from an alkali metal ion or a divalent metal ion; the organic acid is selected from an organic polyacid, a $C_2$-$C_{18}$ linear fatty acid or an aromatic acid. The conjugate salt of N,N-dimethylglycine with metal and organic acid is a conjugate acid salt formed by introducing another organic acid with a hydrophobic group into the salt of N,N-dimethylglycine and a metal ion, so as to modify the hygroscopicity of N,N-dimethylglycine by decreasing the affinity of the salt toward water molecules in the air, or decreasing the affinity or attraction of molecular aggregates formed through crystalline behavior of the salt toward water molecules in the air.

17 Claims, 1 Drawing Sheet

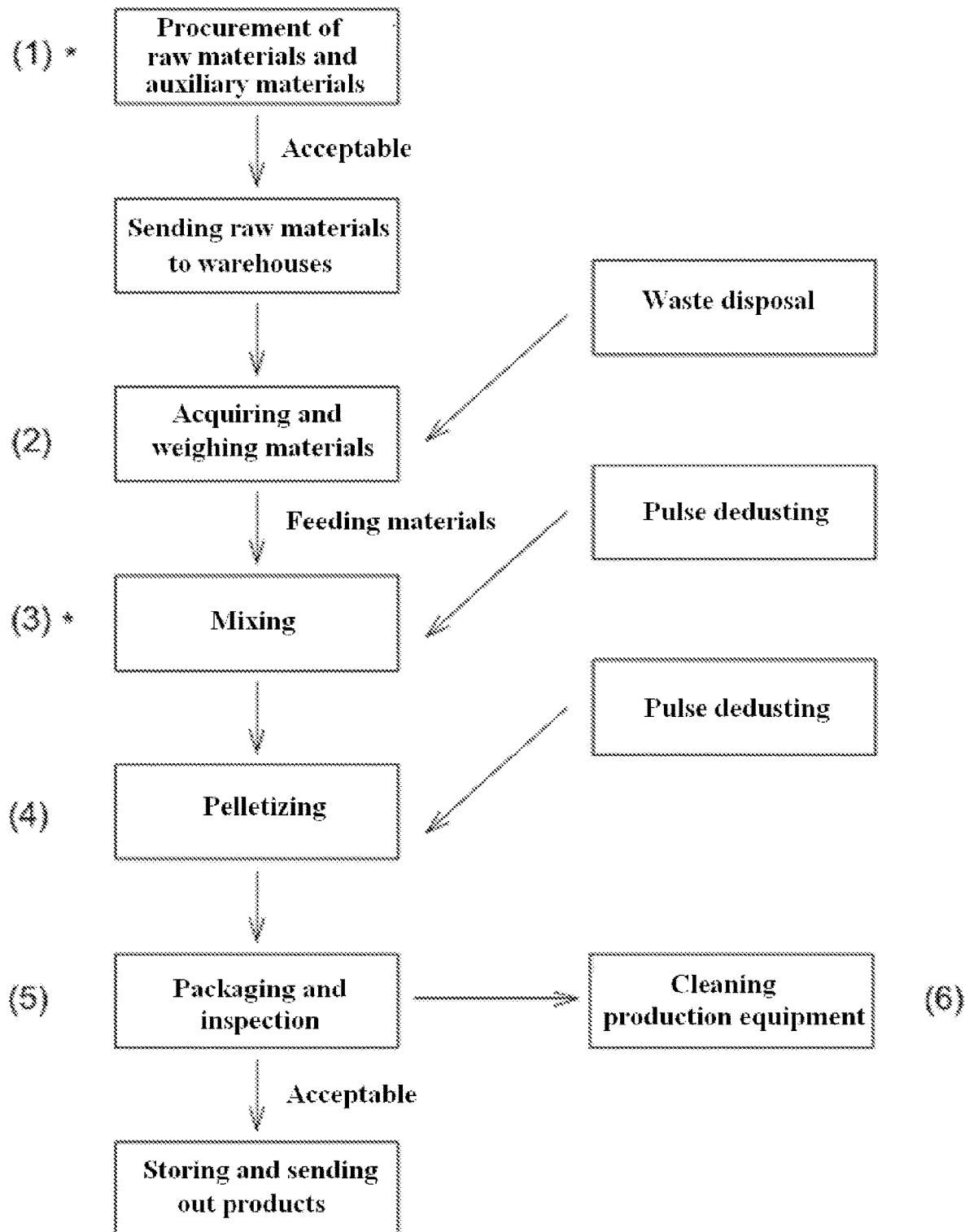

CONJUGATE ACID SALT OF N,N-DIMETHYLGLYCINE WITH ORGANIC ACID, AND COMPOSITION AND USE THEREOF

CROSS REFERENCE TO RELATED APPLICATIONS

This is a U.S. national stage application of the International Patent Application No. PCT/CN2017/109143, filed Nov. 2, 2017, which claims priority to Chinese Patent Application No. 201711010206.2, filed Oct. 25, 2017, both of which are incorporated herein by reference in their entirety.

FIELD OF THE INVENTION

The present invention relates to the field of animal feed additives, and particularly relates to a conjugate acid salt of N,N-dimethylglycine with organic acid, and a composition and use thereof.

BACKGROUND OF THE INVENTION

"Feed additives" refers to substances added in a small amount or trace amount during the processing, production, and use of feed (*Regulations on the Administration of Feeds and Feed Additives*, Order No. 609 of the State Council of the People's Republic of China), including nutritional feed additives and general feed additives also known as non-nutritional feed additives. The nutritional feed additives refer to a small amount or a trace amount of substances added to compound feeds so as to balance feed nutrients, improve feed efficiency, and directly exert nutritional effects on animals, including vitamins, trace elements, amino acids, small peptides and non-protein nitrogen. The general feed additives, also called non-nutritional additives, refer to some non-nutritional substances added to feeds to improve feed efficiency, ensure feed quality, and be beneficial to animal health or metabolism, including growth promoters, deworming agents, feed conditioning agents, feed conditioners, feed preservatives, and Chinese herbal medicine additives. Among them, antibiotics, as feed additives for animal growth-promotion, are widely used and even abused in modern feed processing industries. The antibiotic abuse in both the breeding and pharmaceutical fields has led to the emergence of antibiotic resistance in pathogens and cause a very serious situation. At present, some developed countries such as the European Union, Japan, and the United States have successively issued decisions on banning certain antibiotics in the animal husbandry, and similar work is on the agenda in China. Therefore, to develop new, safe, stable and effective animal feed additives is the key to improving the economic benefits of the animal husbandry. Dimethylglycine (DMG), with a molecular formula as $(CH_3)_2NCH_2COOH$, is white crystals and soluble in water and ethanol. It is a physiologically active nutrient that naturally occurs in food, grains, beans and liver, and is a natural substance occurring in the metabolic pathways of plants and animals. As a nutritional antioxidant additive, dimethylglycine also shows important physiological and biochemical functions in human and animal health. It has been found in a large number of animal tests that dimethylglycine is a very safe food-based nutritional additive.

However, N,N-dimethylglycine is a highly hygroscopic solid, which is difficult to store and use. The commonly used N,N-dimethylglycine hydrochloride, sodium N,N-dimethylglycinate, and potassium N,N-dimethylglycinate also show strong hygroscopicity, and are prone to absorb moisture and deliquesce during storage; thus, high requirements on production equipment and plant facilities shall be established in the product processing, or otherwise the products will absorb moisture and thus agglomerate during the production, failing to meet the application requirements of the feed processing industry. In addition, the packaging of products containing DMG or DMG hydrochloride or alkali metal salt must be tightly sealed; with poor sealing, the product will get moldy and deteriorate due to moisture absorption during storage.

SUMMARY OF THE INVENTION

Provided herein is a conjugate acid salt of N,N-dimethylglycine with a metal and an organic acid, characterized in that, wherein the conjugate acid salt has a following structural formula:

$[(CH_3)_2NCH_2COO]_n M \cdot [\text{Organic acid}]$ wherein n is 1 or 2; M is selected from an alkali metal ion or a divalent metal ion; the organic acid is selected from an organic polyacid, a $C_2$-$C_{18}$ linear fatty acid or an aromatic acid. Also provided herein is a feed composition, comprising at least one of the conjugate acid salt disclosed herein and a carrier acceptable in a pharmaceutical, a foodstuff or a feed. Also provided herein is use of the conjugate acid salt disclosed herein or the feed composition disclosed herein in preparing an animal feed additive or an animal feed.

DETAILED DESCRIPTION OF THE INVENTION

In view of the above, one object of the present invention is to provide a conjugate acid salt of N,N-dimethylglycine with metal and organic acid or a solvate thereof, which is not prone to absorbing moisture.

A specific technical solution is as follows:

A conjugate acid salt of N,N-dimethylglycine with metal and organic acid, having a following structural formula:

$[(CH_3)_2NCH_2COO]_n M \cdot [\text{Organic acid}]$ wherein, n is 1 or 2; M is selected from an alkali metal ion or a divalent metal ion; the organic acid is selected from an organic polyacid, a $C_2$-$C_{18}$ linear fatty acid or an aromatic acid.

In some embodiments, the organic acid is an organic polyacid, and selected from fumaric acid, maleic acid, tartaric acid, succinic acid, malonic acid, malic acid, dihydroxypropionic acid, pyruvic acid, glycolic acid, gluconic acid, galactonic acid, aspartic acid, glutamic acid, citric acid or oxalic acid.

In some embodiments, the organic polyacid is preferably fumaric acid.

In some embodiments, the $C_2$-$C_{18}$ linear fatty acid is a $C_2$-$C_{18}$ linear fatty monoacid, and selected from acetic acid, propionic acid, butyric acid, capric acid, palmitic acid, lauric acid or stearic acid.

In some embodiments, the aromatic acid is selected from benzoic acid, p-toluic acid, naphthoic acid, mandelic acid, p-chlorobenzoic acid, p-bromobenzoic acid, p-aminobenzoic acid, cinnamic acid, salicylic acid, acetylsalicylic acid, p-methylbenzenesulfonic acid or benzenesulfonic acid.

In some embodiments, the aromatic acid is benzoic acid or p-toluic acid.

In some embodiments, the divalent metal ion is selected from Ca(II), Mg(II), Cu(II), Zn(II), Fe(II), Mn(II), Co(II) or Ni(II).

In some embodiments, the conjugate acid salt of N,N-dimethylglycine with metal and organic acid is one of the following salts: $[(CH_3)_2NCH_2COO]_2Ca.[Benzoic\ acid]$, $[(CH_3)_2NCH_2COO]_2Ca.[Fumaric\ acid]$, $[(CH_3)_2NCH_2COO]_2Cu.[Benzoic\ acid]$, $[(CH_3)_2NCH_2COO]_2Cu.[Fumaric\ acid]$, $[(CH_3)_2NCH_2COO]_2Zn.[Benzoic\ acid]$, and $[(CH_3)_2NCH_2COO]_2Zn.[Fumaric\ acid]$. In some embodiments, the N,N-dimethylglycine metal organic acid conjugate acid salt is a solvate, and preferably a hydrate or ethanolate.

Another object of the present invention is to provide use of the above conjugate acid salt of N,N-dimethylglycine with metal and organic acid.

In some embodiments, the conjugate acid salt of N,N-dimethylglycine with metal and organic acid is used in preparing animal feed additives.

In some embodiments, the conjugate acid salt of N,N-dimethylglycine with metal and organic acid is used in preparing animal feeds.

In some embodiments, the animal is selected from poultry, livestock, aquatic animals or pets.

In some embodiments, the poultry are selected from chicken, ducks, geese, or pigeons; the livestock are selected from pigs, cattle, sheep, or horses; the aquatic animal are selected from fish, shrimps, loaches, eels, or crabs.

When used in the breeding of poultry such as chicken, ducks, geese, or pigeons at various growth stages, compared with N,N-dimethylglycine, N,N-dimethylglycine hydrochloride or sodium N,N-dimethylglycinate, the above conjugate acid salt of N,N-dimethylglycine with metal and organic acid presents a more significant improvement effect on poultry production performance, which is reflected in average daily weight gain and feed conversion ratio.

When used in the breeding of livestock such as pigs, cattle, sheep, horses or donkeys, the above conjugate acid salt of N,N-dimethylglycine with metal and organic acid can significantly improve the production performance of farmed animals, which is reflected in average daily weight gain, average daily feed intake and feed efficiency.

When used in the breeding of aquatic animals such as shrimps, fish, loaches, eels, crabs, or *crucians*, the above conjugate acid salt of N,N-dimethylglycine with metal and organic acid can significantly increase the growth rate and anoxic resistance of aquatic animals, alleviating the anoxic harm of aquatic animals and improving their survival rate.

Another object of the present invention is to provide a feed composition.

A feed composition comprises the above conjugate acid salt of N,N-dimethylglycine with metal and organic acid and a carrier acceptable in pharmaceuticals, foodstuffs or feeds.

The carrier includes an excipient, a diluent, an auxiliary agent, a medium, or a combination thereof, which is prepared into a feed additive form such as a tablet, a pill, an emulsion, a capsule, or a premix through a preparation process.

In some embodiments, the feed composition further comprises a nutritional feed additive and/or a non-nutritional feed additive.

The nutritional feed additive is selected from vitamins, proteins, fats, amino acids, cellulose, and mineral trace elements.

The non-nutritional feed additive is selected from growth promoters, deworming agents, feed conditioning agents, feed conditioners, feed preservatives, and Chinese herbal medicine additives.

In some embodiment, the feed composition further comprises a feed raw material.

The present invention provides use of the feed composition comprising the above conjugate acid salt of N,N-dimethylglycine with metal and organic acid.

In some embodiments, the feed composition is used in preparing animal feed additives.

In some embodiments, the feed composition is used in preparing animal feeds.

The animal is a farmed animal, selected from poultry, livestock, aquatic animals or pets.

In another aspect, the present invention further provides a method of improving production performance of farmed animals.

In some embodiments, the method comprises administering the conjugate acid salt of N,N-dimethylglycine with metal and organic acid provided by the present invention to a farmed animal alone with feed.

In some embodiments, the method comprises administering the feed composition comprising the conjugate acid salt of N,N-dimethylglycine with metal and organic acid provided by the present invention to a farmed animal.

The above-mentioned conjugate acid salt of N,N-dimethylglycine with metal and organic acid is a conjugate acid salt formed by introducing another organic acid with a hydrophobic group into the salt of N,N-dimethylglycine and a metal ion, so as to modify the hygroscopicity of N,N-dimethylglycine by decreasing the affinity of the salt toward water molecules in the air, or decreasing the affinity or attraction of molecular aggregates formed through crystalline behavior of the salt toward water molecules in the air. When the conjugate acid salt of N,N-dimethylglycine with metal and organic acid is used in preparing animal feed additives or feeds, the reduction in hygroscopicity makes it possible to lower the damp-proofing requirements on the production equipment of feeds or feed additives and thus reduce the production cost. In addition, the reduction in hygroscopicity of products also lowers the sealing requirements on product packaging, which reduces the cost and avoid the risk of short-term moisture deterioration of the product due to packaging damage caused by accidents during transportation or storage.

In the breeding experiment, the conjugate acid salts of N,N-dimethylglycine with metal and organic acid provided by the present invention showed an improvement effect on the production performance of poultry and livestock equivalent to that of sodium N,N-dimethylglycinate, and some of the salts even showed slightly better improvement effect.

BRIEF DESCRIPTION OF THE DRAWINGS

The FIGURE is a flow chart for the production of a hybrid pellet feed additive.

DETAILED DESCRIPTION OF THE EMBODIMENTS

In order to facilitate understanding of the present invention, the present invention will be described more fully below. However, the present invention can be implemented in many different forms and is not limited to the embodiments described herein. Rather, these embodiments are provided to enable a thorough understanding of the present disclosure.

Unless defined otherwise, all technical and scientific terms used herein have the same meaning as commonly understood by one of ordinary skill in the art to which this invention belongs. The terminology used herein in the description of the invention is for the purpose of describing particular embodiments only and is not intended to limit the invention.

The present invention provides a conjugate acid salt of N,N-dimethylglycine with metal and organic acid, having a following structural formula:

[(CH$_3$)$_2$NCH$_2$COO]$_n$M.[Organic acid]

wherein, n is 1 or 2; M is selected from an alkali metal ion or a divalent metal ion; the organic acid is selected from an organic polyacid, a C$_2$-C$_{18}$ linear fatty acid or an aromatic acid.

The M involved in the present invention represents a metal ion.

The divalent metal ion involved in the present invention includes alkaline earth metal ions or other divalent metal ions.

The alkali metal ion involved in the present invention refers to a +1 cation formed by the group IA elements, such as sodium, potassium, rubidium, cesium and rubidium, losing an electron in a chemical reaction.

The alkaline earth metal ions involved in the present invention refer to +2 cations formed by the group IIA elements, such as beryllium, magnesium, calcium, strontium, barium, and radium, losing electrons in a chemical reaction, which are respectively Ca(II), Mg(II), Ba(II) or Sr(II).

The other divalent metal ions involved in the present invention include transition metal divalent ion, and may be selected from Cu(II), Zn(II), Fe(II), Cd(II), Co(II) or Ni(II).

Expression of some compounds involved in the present invention: the term "C$_2$-C$_{18}$ linear fatty acid" represents a linear fatty acid having 2-18 carbon atoms; the term "C$_2$-C$_{18}$ linear fatty monoacid" represents a fatty acid having 2-18 carbon atoms and only one carboxyl group.

The term "conjugate acid salt" in the present invention refers to a salt formed by an anion, which is formed by an organic acid donating a proton, and a cation, which is formed by an N,N-dimethylglycinate metal salt accepting the proton from the organic acid.

The method of preparing, isolating, and purifying the conjugate acid salt of N,N-dimethylglycine with metal and organic acid comprises the following steps:

(1) successively adding N,N-dimethylglycine hydrochloride and a water-soluble solvent into a reactor, and stirring vigorously at room temperature to form a suspension;

(2) adding an alkali metal hydroxide or divalent metal hydroxide to the suspension or adding a divalent metal halide under an alkaline condition to the suspension, and stirring at room temperature;

(3) dissolving an organic acid in a water-soluble solvent, introducing to the reaction solution obtained in step (2), and stirring to allow reaction for 30-60 minutes;

(4) subjecting the reaction product obtained in step (3) to suction filtration, and drying the filter cake under reduced pressure at 100-110° C., so as to obtain the conjugate acid salt of N,N-dimethylglycine with metal and organic acid.

In some embodiments, the water-soluble solvent is selected from absolute ethanol, methanol, i-propanol, n-butanol, or tetrahydrofuran.

In some embodiments, the alkali metal hydroxide may be selected from sodium hydroxide or potassium hydroxide.

In some embodiments, the divalent metal hydroxide is an alkaline earth metal hydroxide. Specifically, the alkaline earth metal hydroxide is calcium hydroxide (Ca(OH)$_2$), magnesium hydroxide (Mg(OH)$_2$), barium hydroxide (Ba(OH)$_2$), or strontium hydroxide (S(OH)$_2$), wherein the metal ion M of the corresponding product [(CH$_3$)$_2$NCH$_2$COO]$_n$M.[Organic acid] is a divalent alkaline earth metal ion, and may be selected from Ca (II), Mg (II), Ba (II), or Sr (II).

In some embodiments, the divalent metal hydroxide is an alkaline transition metal hydroxide. Specifically, the alkaline transition metal hydroxide is copper hydroxide (Cu(OH)$_2$), zinc hydroxide (Zn(OH)$_2$), ferrous hydroxide (Fe(OH)$_2$), hydroxide cadmium (Cd(OH)$_2$), cobalt hydroxide (Co(OH)$_2$) or nickel hydroxide (Ni(OH)$_2$), wherein the metal ion M of the corresponding product [(CH$_3$)$_2$NCH$_2$COO]$_n$M.[Organic acid] is a transition metal divalent ion, and may be selected from Cu (II), Zn (II), Fe (II), Cd (II), Co (II), or Ni (II).

In some embodiments, in the step of adding the divalent metal halide under an alkaline condition to the suspension in step (2), the alkaline condition refers to that sufficient sodium hydroxide is added to the reaction system so that the pH value of the reaction system is 7 to 8.

The polyvalent metal chloride is specifically copper chloride (CuCl$_2$), zinc chloride (ZnCl$_2$), manganese chloride (MnCl$_2$), ferrous chloride (FeCl$_2$), chromous chloride (CrCl$_2$), cadmium chloride (CdCl$_2$), cobalt chloride (CoCl$_2$) or nickel chloride (NiCl$_2$).

The polyvalent metal bromide is specifically copper bromide (CuBr$_2$), zinc bromide (ZnBr$_2$), manganese bromide (MnBr$_2$), ferrous bromide (FeBr$_2$), chromous bromide (CrBr$_2$), cadmium bromide (CdBr$_2$), cobalt bromide (CoBr$_2$), or nickel bromide (NiBr$_2$).

The polyvalent metal iodide is specifically copper bromide (CuI$_2$), zinc iodide (ZnI$_2$), manganese iodide (MnI$_2$), ferrous iodide (FeI$_2$), chromous iodide (CrI$_2$), and cadmium iodide (CdI$_2$), cobalt iodide (CoI$_2$), or nickel iodide (NiI$_2$).

The metal ion contained in the product [(CH$_3$)$_2$NCH$_2$COO]$_n$M.[Organic acid] formed in the above process is Cu(II), Zn(II), Fe(II), Mn(II), Cr(II), Cd(II), Co(II) or Ni(II).

In some embodiments, the organic acid dissolved in the water-soluble solvent in step (3) may be selected from an organic polyacid, a linear fatty monoacid, or an aromatic organic acid.

The organic polyacid may be selected from fumaric acid, maleic acid, tartaric acid, succinic acid, malonic acid, malic acid, dihydroxypropionic acid, pyruvic acid, glycolic acid, glucuronic acid, galacturonic acid, aspartic acid, glutamic acid, citric acid or oxalic acid, and preferably fumaric acid.

The linear fatty monoacid may be selected from a C$_4$-C$_{18}$ linear fatty monoacid, and preferably tetradecanoic acid.

The aromatic organic acid may be selected from benzoic acid, p-toluic acid, p-chlorobenzoic acid, p-bromobenzoic acid, p-aminobenzoic acid, mandelic acid, cinnamic acid, benzenesulfonic acid, p-methylbenzenesulfonic acid, naphthoic acid, salicylic acid or acetylsalicylic acid, and preferably benzoic acid, p-toluic acid or p-methylbenzenesulfonic acid.

In some embodiments, in order to obtain a conjugate acid salt of N,N-dimethylglycine with metal and organic acid with higher chemical purity and lower impurity content, the crude product is recrystallized, under appropriate temperature, illumination and mechanical vibration conditions in an alcohol solvent, an alcohol-water mixed solvent or other organic solvents that can be used for product recrystallization, and separated to obtain a conjugate acid salt of N,N-dimethylglycine with metal and organic acid with a certain crystalline state. The said conjugate acid salt of N,N-dimethylglycine with metal and organic acid with a certain crystalline state may be a solvate thereof.

The term "solvate" involved in the present invention refers to a co-crystallizing complex formed by the conjugate acid salt combining with solvent molecules in a chemical equivalent or non-chemical equivalent amount through non-covalent intermolecular forces caused by external conditions and internal conditions during the process of contacting the conjugate acid salt with the solvent molecules. Solvents for forming the solvate include but not limited to water, acetone, ethanol, methanol, dimethyl sulfoxide, ethyl acetate, acetic acid, and i-propanol. "Hydrate" refers to a complex or crystal formed when the solvent molecules are water, i.e., a compound formed by combining with water in a chemical equivalent or non-chemical equivalent amount through non-covalent intermolecular forces.

In some embodiments, a solvate of the conjugate acid salt of N,N-dimethylglycine with metal and organic acid may be selected from a hydrate or ethanolate of the conjugate acid salt of N,N-dimethylglycine with metal and organic acid.

In one specific embodiment, the conjugate acid salt of N,N-dimethylglycine with metal and organic acid is $[(CH_3)_2NCH_2COO]_2Ca \cdot [Benzoic\ acid]$.

In one specific embodiments, the conjugate acid salt of N,N-dimethylglycine with metal and organic acid is $[(CH_3)_2NCH_2COO]_2Ca \cdot [Fumaric\ acid]$.

In one specific embodiment, the conjugate acid salt of N,N-dimethylglycine with metal and organic acid is $[(CH_3)_2NCH_2COO]_2Cu \cdot [Benzoic\ acid]$.

In one specific embodiments, the conjugate acid salt of N,N-dimethylglycine with metal and organic acid is $[(CH_3)_2NCH_2COO]_2Cu \cdot [Fumaric\ acid]$.

In one specific embodiment, the conjugate acid salt of N,N-dimethylglycine with metal and organic acid is $[(CH_3)_2NCH_2COO]_2Zn \cdot [Benzoic\ acid]$.

In one specific embodiments, the conjugate acid salt of N,N-dimethylglycine with metal and organic acid is $[(CH_3)_2NCH_2COO]_2Zn \cdot [Fumaric\ acid]$.

The present invention provides a high-humidity stability study of the above-mentioned conjugate acid salt of N,N-dimethylglycine with metal and organic acid. In the high-humidity stability test study prescribed by the new stability test standard for feed additives, the conjugate acid salt of N,N-dimethylglycine with metal and organic acids were placed at 25° C. and RH 95% and all showed a hygroscopic weight gain of less than 5% at day 10, satisfying the requirements of feed additives on humidity.

The term "and/or" used herein includes any and all combinations of one or more of the associated listed items.

The present invention involves the use of the above conjugate acid salts of N,N-dimethylglycine with metal and organic acid in preparing animal feed additives or animal feeds.

The term "animal" involved in the present invention refers to human or farmed animals that cannot synthesize organic matters from inorganic matters, but can only utilize organic matters as food in order to perform vital activities such as ingestion, digestion, absorption, breathing, circulation, excretion, sensation, exercise, and reproduction.

Optionally, the farmed animals include poultry, livestock, aquatic animals, and other farmed and legally captured animals including pets. Specifically, the poultry involved in the present invention are edible animals such as chicken, ducks, geese, pigeons, quails or turkeys at various growth stages; the livestock involved in the present invention are edible animals such as pigs, cattle, sheep, rabbits, and horses at various growth stages; the aquatic animals involved in the present invention are fish, shrimps, loaches, crabs or eels at each growth stage; the pets involved in the present invention include, but are not limited to, cats, dogs, and rabbits.

In some breeding schemes, addition of the conjugate acid salts of N,N-dimethylglycine with metal and organic acid provided by the present invention into the basic diets of poultry such as chicken, ducks, geese or pigeons, can significantly reduce the feed conversion ratio and improve the feed efficiency for poultry, showing an effect equivalent to that of N,N-dimethylglycine.

In some breeding schemes, addition of the conjugate acid salts of N,N-dimethylglycine with metal and organic acid provided by the present invention into the basic diets of monogastric or ruminant livestock such as pigs, cattle, and sheep, shows significant improvement effect on the production performance of the livestock, which is illustrated by the average daily weight gain and decrease in average feed conversion ratio.

In some breeding schemes, addition of the conjugate acid salts of N,N-dimethylglycine with metal and organic acid provided by the present invention into the basic diets of aquatic animals such as fish and shrimps, can significantly improve anoxic resistance and survival rate of the aquatic animals, especially fish.

In some breeding schemes, the conjugate acid salts of N,N-dimethylglycine with metal and organic acid can be applied in combination with pet food such as cat food and dog food to realize the effect of regulating the gastrointestinal function of pets such as cats and dogs and effectively relieve diarrhea symptoms caused by indigestion in pets.

Therefore, the non-hygroscopic conjugate acid salts of N,N-dimethylglycine with metal and organic acid meet the requirements of novel feed additives for high humidity stability and present an improvement effect on the production performance of farmed animals similar to or higher than that of sodium N,N-dimethylglycinate, thus can be used in the preparation of animal feed additives or animal feed.

The present invention provides a feed composition, comprising at least one of the conjugate acid salts of N,N-dimethylglycine with metal and organic acid provided by the present invention and an auxiliary material usable for feed.

The term "composition" involved in the present invention refers to a collective of compounds including one or more compounds as an active ingredient.

The term "comprise (or comprises, comprised, comprising)" in the present invention is open-ended, which includes the content explicitly referred to in the present invention, but does not exclude the content of other aspects.

Optionally, the auxiliary material usable for feed includes a feed additive or a carrier, a binder, an anti-caking agent, a stabilizer, an emulsifier, a diluent, a medium, or a combination thereof that is commonly used in feed.

The term "carrier" involved in the present invention refers to a substance useable for feed and capable of carrying an active ingredient, improving dispersibility thereof, and having high chemical stability and adsorption, and includes organic carriers or inorganic carriers. The organic carriers are generally materials containing a lot of crude fibers, including but not limited to corn flour, corn cob flour, wheat bran, rice hull flour, defatted rice bran, rice bran and hull, corn stalk flour, and peanut hull flour. The inorganic carriers are generally minerals, mainly include calcium salts and silicon oxides, and are used for the preparation of trace element premixes, including but not limited to calcium carbonate, silicate, vermiculite, zeolite, and sepiolite.

The term "diluent" involved in the present invention refers to a substance that evenly distributes additive raw materials in other materials, and dilutes high-concentration additive raw materials into low-concentration premixed agents or premixes; it can separate trace components from each other and reduce the interaction between active ingredients, so as to increase the stability of the active ingredients without affecting the physical and chemical properties thereof. Diluents include organic diluents and inorganic diluents. Common organic diluents include, but are not limited to, corn flour, degermed corn flour, dextrose (glucose), sucrose, semolina with bran, stir-fried soybean powder, wheat middling, and corn gluten meal. Commonly used inorganic diluents include but are not limited to limestone, calcium dihydrogen phosphate, shell powder, kaolin (white clay), salt and sodium sulfate.

Auxiliary agents involved in the present invention include, but are not limited to, binders, wetting agents, disintegrants, lubricants, antioxidants, and preservatives.

The term "medium" involved in the present invention refers to solvents required for dissolving or dispersing solids, which include, but are not limited to, water, ethanol, and glycerin.

Further, the feed composition comprises an additional animal feed additive, and the additional animal feed is selected from a nutritional feed additive, a general feed additive or a medicinal feed additive.

Specifically, the nutritional feed additive includes, but is not limited to, amino acids, amino acid salts and their analogues, vitamins and vitamin-like substances, mineral elements and their complexes (chelates), microbial enzyme preparations, or non-protein nitrogen; the general feed additive includes, but is not limited to, growth promoters, deworming agents, flavorings and attractants, feed conditioning agents, feed conditioners, feed preservatives, and Chinese herbal medicine additives; the medicinal feed additive includes, but is not limited to, a veterinary drug premix which has the function of preventing animal diseases and promoting animal growth and can be added to the feed for a long period of time and incorporated into a carrier or diluent.

Further, the feed composition may include a feed raw material, the feed raw material being selected from animal, plant, microbial and mineral non-feed-additive substances that are usable for feed and can be used to prepare feed.

In some embodiments, the feed composition is an additive-premixed feed, a concentrated feed, a compound feed, or a concentrate supplement.

The additive-premixed feed refers to a uniform mixture prepared by mixing nutritional feed additive, which comprises any two or more of mineral trace elements, vitamins, microorganisms, and amino acids, with the butyryl glutamic acid derivative provided by the present invention or other feed additives, carriers and/or diluents according to a certain proportion, wherein the nutritional feed additive is present in a content that can meet the basic nutritional requirements of an applicable animal within its specific physiological stage, and is not less than 0.1% and not more than 10% in the compound feed, concentrate supplement or animal drinking water.

The concentrated feed refers to a feed mainly composed of proteins, minerals and feed additives according to a certain proportion.

The compound feed refers to a feed prepared by mixing a variety of feed raw materials and feed additives according to a certain proportion depending on the nutritional needs of the farmed animals.

The concentrate supplement refers to a feed prepared by mixing a variety of feed raw materials and feed additives according to a certain proportion in order to supplement nutrition to herbivores.

The invention also involves a preparation process of the feed composition, comprising weighing the raw materials and auxiliary materials, mixing by a mixing unit, pelletizing, quality inspection and packaging.

I. Preparation of Conjugate Acid Salts of N,N-Dimethylglycine with Metal and Organic Acid Embodiment 1

Conjugate Acid Salt of Calcium N,N-Dimethylglycinate with Benzoic Acid

The chemical formula is $[(CH_3)_2NCH_2COO^-]_2Ca^{2+}(PhCOOH)_2$, and the structural formula is as follows:

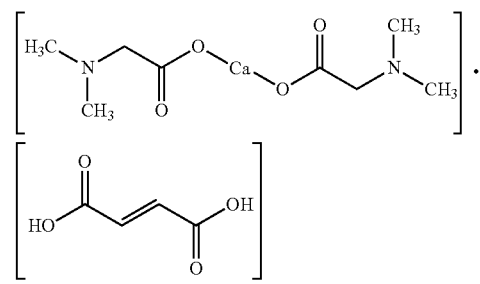

Steps of Preparation

Step 1: Preparation of N,N-Dimethylglycine Hydrochloride 275 mL (40%, 2.44 mol, 4.6 eq) of dimethylamine aqueous solution was added to a three-neck flask. Under mechanical stirring in a low-temperature reaction tank, 50 mL (50.0 g/50 ml, 0.53 mol, 1.0 eq) of chloroacetic acid aqueous solution was slowly added dropwise through a pressure-equalizing dropping funnel wherein the flow rate of chloroacetic acid aqueous solution was controlled so that the temperature of the reaction system did not exceed 50.0° C., followed by a reaction at room temperature for 11 hours. Then the solution was subjected to vacuum concentration to remove unreacted dimethylamine and water to give 50 mL of a crude N,N-dimethylglycine aqueous solution. The crude N,N-dimethylglycine aqueous solution was stirred at 0° C. in the low-temperature reaction tank, and the concentrated hydrochloric acid was slowly added dropwise to the reaction system until the pH 1-2. The reaction system was stirred for 10 minutes to precipitate a large amount of white flocculent solid. The reaction system was then added with 40 mL of absolute ethanol and then stirred at 0° C. for 20 minutes. The reaction mixture was filtered while it was still cool. The filter cake was dried under reduced pressure in an oven at 50° C. overnight to give N,N-dimethylglycine hydrochloride which was a white powdery crystal (52.3 g, 70.7%).

Step 2: Preparation of Conjugate Acid Salt of Calcium N,N-Dimethylglycinate with Benzoic Acid 20.0 g (143.3 mmol, 1.00 eq) of N,N-dimethylglycine hydrochloride and 250 mL of absolute ethanol were successively added into a 1 L three-neck flask with vigorous stirring at room temperature to form a uniform suspension. 6.0 g of solid sodium hydroxide was added in batches (1 g×6, 150.0 mmol, 1.05 eq) into the reaction system with heat releasing, and the resulting reaction system was stirred at room temperature for 0.5 hour. 5.31 g (771.64 mmol, 0.50 eq) of powdery solid calcium hydroxide was added into the reaction system and the resulting reaction mixture was vigorously stirred at room temperature for 2.0 hours to give a viscous reaction solution. 17.50 g (143.3 mmol, 0.50 eq) of benzoic acid in 60 mL of absolute ethanol was added into the reaction system and the resulting reaction mixture was stirred for 3.0 hours to give a white suspension. The white suspension was subjected to suction filtration, and the filter cake was dried under reduced pressure in an oven at 105° C. overnight to give the product as an off-white powdery solid (19.77 g, 56.6%).

Embodiment 2

Conjugate Acid Salt of Calcium N,N-Dimethylglycinate with Fumaric Acid

The chemical formula is $[(CH_3)_2NCH_2COO^-]_2Ca^{2+}$ (COOHCHCHCOOH), and the structural formula is as follows:

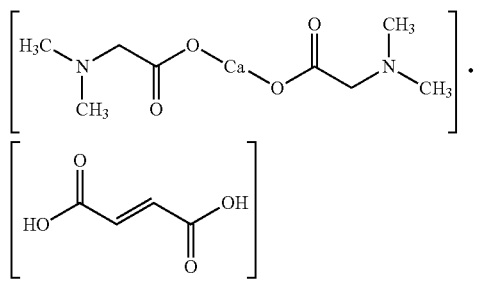

20.0 g (143.3 mmol, 1.00 eq) of N,N-dimethylglycine hydrochloride and 250 mL of absolute ethanol were successively added into a 1 L three-neck flask with vigorous stirring at room temperature to form a uniform suspension. 5.80 g of solid sodium hydroxide was added in batches (1 g×6, 145.0 mmol, 1.00 eq) into the reaction system with heat releasing, and the resulting reaction system was stirred at room temperature for 0.5 hour. 5.35 g (72.35 mmol, 0.50 eq) of powdery solid calcium hydroxide was added into the reaction system and the resulting reaction mixture was vigorously stirred at room temperature for 2.0 hours to give a viscous reaction solution. 8.35 g (71.94 mmol, 0.50 eq) of fumaric acid in 60 mL of absolute ethanol was added into the reaction system and the resulting reaction mixture was stirred for 3.0 hours to give a white suspension. The white suspension was subjected to suction filtration, and the filter cake was dried under reduced pressure in an oven at 105° C. overnight to give the product as an off-white powdery solid (16.03 g, 62.10%).

Embodiment 3

Conjugate Acid Salt of Calcium N,N-Dimethylglycinate with Tetradecanoic Acid

The chemical formula is $[(CH_3)_2NCH_2COO^-]_2Ca^{2+}$ $(CH_3(CH_2)_{12}COOH)_2$, and the structural formula is as follows:

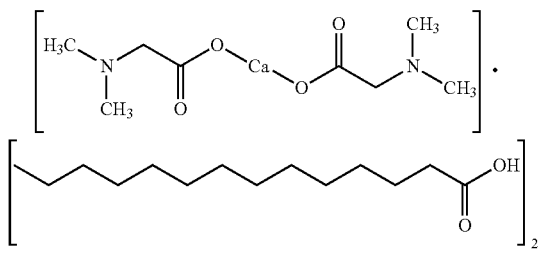

20.0 g (143.3 mmol, 1.00 eq) of N,N-dimethylglycine hydrochloride and 250 mL of absolute ethanol were successively added into a 1 L three-neck flask with vigorous stirring at room temperature to form a uniform suspension. 6.0 g of solid sodium hydroxide was added in batches (1 g×6, 150.0 mmol, 1.05 eq) into the reaction system with heat releasing, and the resulting reaction system was stirred at room temperature for 0.5 hour. 5.30 g (71.64 mmol, 0.50 eq) of powdery solid calcium hydroxide was added into the reaction system and the resulting reaction mixture was vigorously stirred at room temperature for 2.0 hours to give a viscous reaction solution. 16.36 g (71.64 mmol, 0.50 eq) of tetradecanoic acid in 75 mL of absolute ethanol was added into the reaction system and the resulting reaction mixture was stirred for 3.0 hours to give a white suspension. The white suspension was subjected to suction filtration, and the filter cake was dried under reduced pressure in an oven at 105° C. overnight to give the product as an off-white powdery solid (23.05 g, 45.90%).

Embodiment 4

Conjugate Acid Salt of Copper N,N-Dimethylglycinate with Benzoic Acid

The chemical formula is $[(CH_3)_2NCH_2COO^-]_2Cu^{2+}$ $(PhCOOH)_2$, and the structural formula is as follows:

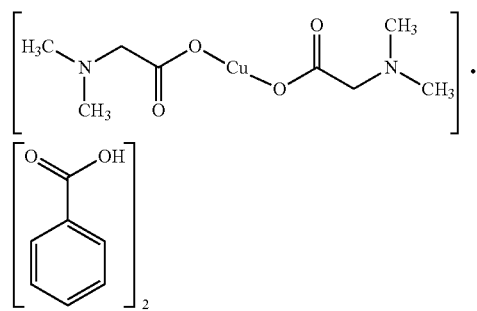

20.0 g (143.3 mmol, 1.00 eq) of N,N-dimethylglycine hydrochloride and 250 mL of absolute ethanol were successively added into a 1 L three-neck flask with vigorous stirring at room temperature to form a uniform suspension. 5.73 g of solid sodium hydroxide was added in batches (1 g×6, 143.3 mmol, 1.00 eq) into the reaction system with heat releasing, and the resulting reaction system was stirred at room temperature for 0.5 hour. 7.00 g (75.6 mmol, 0.53 eq) of powdery copper hydroxide was added into the reaction system and the resulting reaction mixture was vigorously stirred at room temperature for 2.0 hours to give a viscous reaction solution. 17.50 g (143.3 mmol, 0.50 eq) of benzoic acid in 60 mL of absolute ethanol was added into the reaction system and the resulting reaction mixture was stirred for 3.0 hours to give a white suspension. The white suspension was subjected to suction filtration, and the filter cake was dried under reduced pressure in an oven at 105° C. overnight to give the product as an off-white powdery solid (18.93 g, 51.70%).

Embodiment 5

Conjugate Acid Salt of Copper N,N-Dimethylglycinate with Fumaric Acid

The chemical formula is $[(CH_3)_2NCH_2COO^-]_2Cu^{2+}$ (COOHCHCHCOOH), and the structural formula is as follows:

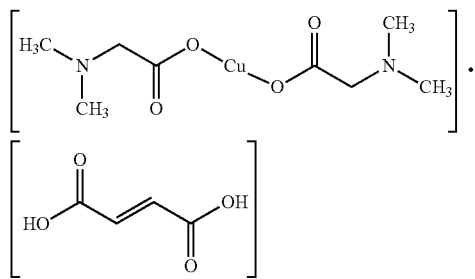

20.0 g (143.3 mmol, 1.00 eq) of N,N-dimethylglycine hydrochloride and 250 mL of absolute ethanol were successively added into a 1 L three-neck flask with vigorous stirring at room temperature to form a uniform suspension. 5.75 g of solid sodium hydroxide was added in batches (1 g×6, 143.8 mmol, 1.00 eq) into the reaction system with heat releasing, and the resulting reaction system was stirred at room temperature for 0.5 hour. 7.00 g (71.65 mmol, 0.50 eq) of powdery solid copper hydroxide was added into the reaction system and the resulting reaction mixture was vigorously stirred at room temperature for 2.0 hours to give a viscous reaction solution. 8.32 g (71.64 mmol, 0.50 eq) of fumaric acid in 60 mL of absolute ethanol was added into the reaction system and the resulting reaction mixture was stirred for 3.0 hours to give a white suspension. The white suspension was subjected to suction filtration, and the filter cake was dried under reduced pressure in an oven at 105° C. overnight to give the product as an off-white powdery solid (12.90 g, 46.9%).

Embodiment 6

Conjugate Acid Salt of Zinc N,N-Dimethylglycinate with Benzoic Acid

The chemical formula is $[(CH_3)_2NCH_2COO^-]_2Zn^{2+}$ (PhCOOH)$_2$, and the structural formula is as follows:

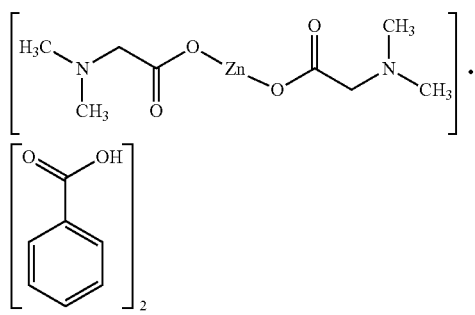

20.0 g (143.3 mmol, 1.00 eq) of N,N-dimethylglycine hydrochloride and 250 mL of absolute ethanol were successively added into a 1 L three-neck flask with vigorous stirring at room temperature to form a uniform suspension. 6.0 g of solid sodium hydroxide was added in batches (1 g×6, 150.0 mmol, 1.05 eq) into the reaction system with heat releasing, and the resulting reaction system was stirred at room temperature for 0.5 hour. 7.20 g (72.44 mmol, 0.50 eq) of powdery solid zinc hydroxide was added into the reaction system and the resulting reaction mixture was vigorously stirred at room temperature for 2.0 hours to give a viscous reaction solution. 17.50 g (143.30 mmol, 0.50 eq) of benzoic acid in 60 mL of absolute ethanol was added into the reaction system and the resulting reaction mixture was stirred for 3.0 hours to give a white suspension. The white suspension was subjected to suction filtration, and the filter cake was dried under reduced pressure in an oven at 105° C. overnight to give the product as an off-white powdery solid (15.36 g, 41.8%).

Embodiment 7

Conjugate Acid Salt of Zinc N,N-Dimethylglycinate with Fumaric Acid

The chemical formula is $[(CH_3)_2NCH_2COO^-]_2Zn^{2+}$ (COOHCHCHCOOH), and the structural formula is as follows:

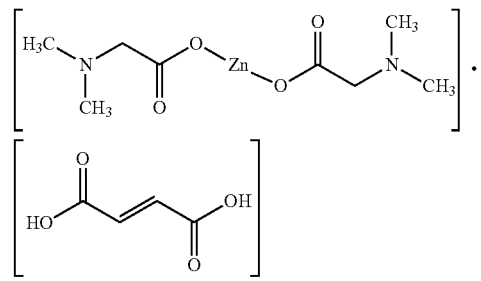

20.0 g (143.3 mmol, 1.00 eq) of N,N-dimethylglycine hydrochloride and 250 mL of absolute ethanol were successively added into a 1 L three-neck flask with vigorous stirring at room temperature to form a uniform suspension. 5.75 g of solid sodium hydroxide was added in batches (1 g×6, 143.76 mmol, 1.00 eq) into the reaction system with heat releasing, and the resulting reaction system was stirred at room temperature for 0.5 hour. 7.12 g (71.64 mmol, 0.50 eq) of powdery solid zinc hydroxide was added into the reaction system and the resulting reaction mixture was vigorously stirred at room temperature for 2.0 hours to give a viscous reaction solution. 8.30 g (71.51 mmol, 0.50 eq) of fumaric acid in 60 mL of absolute ethanol was added into the reaction system and the resulting reaction mixture was stirred to allow reaction for 3.0 hours to give a white suspension. The white suspension was subjected to suction filtration, and the filter cake was dried under reduced pressure in an oven at 105° C. overnight to give the product as an off-white powdery solid (12.49 g, 45.2%).

II. Related Properties of Conjugate Acid Salts of N,N-Dimethylglycine with Metal and Organic Acid Test samples and suppliers are as follows:
Sample 1: N,N-dimethylglycine hydrochloride, from J&K Scientific Ltd.
Sample 2: Sodium N,N-dimethylglycinate, from Shandong Xiya Chemical Industry Co., Ltd.

Sample 3: Calcium N,N-dimethylglycinate, from R&D center of Guangzhou Insighter Biotechnology Co., Ltd.

Sample 4: Calcium benzoate, from R&D center of Guangzhou Insighter Biotechnology Co., Ltd.

Sample 5: Conjugate acid salt of calcium N,N-dimethylglycinate with benzoic acid, prepared in Embodiment 1.

Sample 6: Conjugate acid salt of calcium N,N-dimethylglycinate with fumaric acid, prepared in Embodiment 2.

Sample 7: Conjugate acid salt of calcium N,N-dimethylglycinate with tetradecanoic acid, prepared in Embodiment 3.

Sample 8: Conjugate acid salt of copper N,N-dimethylglycinate with benzoic acid, prepared in Embodiment 4.

Sample 9: Conjugate acid salt of copper N,N-dimethylglycinate with fumaric acid, prepared in Embodiment 5.

Sample 10: Conjugate acid salt of zinc N,N-dimethylglycinate with benzoic acid, prepared in Embodiment 6.

Sample 11: Conjugate acid salt of zinc N,N-dimethylglycinate with fumaric acid, prepared in Embodiment 7.

1. Appearance and Melting Point Determination

TABLE 1

Appearance and melting point determination of conjugate acid salts of N,N-dimethylglycine with metal and organic acid

| Test sample | Appearance | Melting point/° C. |
|---|---|---|
| N,N-dimethylglycine hydrochloride | White crystalline particles | 189-193 |
| Sodium N,N-dimethylglycinate | White powders | 217° C. |
| Calcium N,N-dimethylglycinate | White powders | 220° C., not melted, decomposed |
| Calcium benzoate | White powders | >260° C., not melted, not decomposed |
| Sample 5 | White powders | >245° C. not melted, decomposed |

2. High-Humidity Stability Test

Method: A $KNO_3$ saturated solution (25° C., RH 90%) was placed in the lower part of a constant-temperature and constant-humidity sealed container. The test samples, three parallels for each test sample, were placed at 25° C. and RH 95%±1% for 10 days, and their average weight gains were measured at day 5 and day 10.

Results: The test data was statistically analyzed using SPSS18 software. The test results are expressed as "mean value±standard error" as shown in Table 2. At 25° C. and RH 95%, the sample 1, sample 2, and sample 3, which were respectively hydrochloride, sodium salt and calcium salt of DMG, showed very high hygroscopicity, the weight gains of the test samples at day 5 turned the samples into water-like status. Samples 5-11 were respectively N,N-dimethylglycine organic acid calcium salt, N,N-dimethylglycine organic acid copper salt or N,N-dimethylglycine organic acid zinc salt, showing a hygroscopic weight gain of no higher than 3.7% at day 5, and no significant difference in hygroscopic weight gain were observed between day 5 and day 10.

Conclusion: After placed for 10 days under a constant-temperature and constant-humidity condition of 25° C. and RH 95%±1%, all the N,N-dimethylglycine metal organic acid conjugate acid salts showed a hygroscopic weight gain of lower than 5% and relative stability, satisfying the requirements of feed additives on humidity.

TABLE 2

High-humidity stability study of conjugate acid salts of N,N-dimethylglycine with metal and organic acid

| Compound | Day 5 (%) | Day 10 (%) |
|---|---|---|
| Sample 1 | 79.86 ± 0.94 | 80.69 ± 0.59 |
| Sample 2 | 49.09 ± 1.14 | 52.44 ± 0.48 |
| Sample 3 | 38.40 ± 0.22 | 41.83 ± 0.35 |
| Sample 5 | 3.67 ± 0.41 | 3.69 ± 0.28 |
| Sample 6 | 3.11 ± 0.23 | 3.21 ± 0.07 |
| Sample 7 | 2.41 ± 0.04 | 3.06 ± 0.29 |
| Sample 8 | 2.51 ± 0.07 | 2.90 ± 0.09 |
| Sample 9 | 2.74 ± 0.10 | 2.90 ± 0.05 |
| Sample 10 | 3.02 ± 0.15 | 3.65 ± 0.08 |
| Sample 11 | 2.39 ± 0.12 | 2.88 ± 0.22 |

III. Preparation Method of Feed Composition

The conjugate acid salts of N,N-dimethylglycine with metal and organic acid of embodiment 1-7 were respectively mixed with a corresponding auxiliary material to prepare a corresponding hybrid pellet feed additive.

1. Materials

Raw materials: The conjugate acid salts of N,N-dimethylglycine with metal and organic acid of embodiment 1-7, and sodium N,N-dimethylglycinate.

Carrier: Corn starch.

Binder: 1.3% hydroxypropyl methyl cellulose aqueous solution.

2. Product Formula

TABLE 3

Formula of hybrid pellet feed additives of conjugate acid salts of N,N-dimethylglycine with metal and organic acid

| Product name | Raw material/parts by mass | Carrier/ parts by mass | Binder/ parts by mass |
|---|---|---|---|
| Reference 1 | Sodium N,N-dimethylglycinate 20 | 80 | 35 |
| Product 1 | Conjugate acid salt of calcium N,N-dimethylglycinate with benzoic acid 20 | 80 | 35 |
| Product 2 | Conjugate acid salt of calcium N,N-dimethylglycinate with fumaric acid 20 | 80 | 35 |
| Product 3 | Conjugate acid salt of calcium N,N-dimethylglycinate with tetradecanoic acid 20 | 80 | 35 |
| Product 4 | Conjugate acid salt of copper N,N-dimethylglycinate with benzoic acid 20 | 80 | 35 |
| Product 5 | Conjugate acid salt of copper N,N-dimethylglycinate with fumaric acid 20 | 80 | 35 |
| Product 6 | Conjugate acid salt of zinc N,N-dimethylglycinate with benzoic acid 20 | 80 | 35 |
| Product 7 | Conjugate acid salt of zinc N,N-dimethylglycinate with fumaric acid 20 | 80 | 35 |

3. Production Process

Production process of the hybrid pellet feed additive involved in the present invention is described below in combination with The FIGURE.

Raw material supply: The raw materials were supplied by the R&D center of Guangzhou Insighter Biotechnology Co., Ltd., and inspected by the quality control department as acceptable products with a purity of >99%.

Procurement of auxiliary materials: The auxiliary materials were purchased from qualified suppliers. After determined to be acceptable by sampling inspection, the auxiliary materials were sent to warehouses and stored for later use. This step is a key control point that quality of the auxiliary materials must be strictly controlled.

Acquiring and weighing materials: The raw materials and the auxiliary materials were successively weighed and double-checked according to the proportions in the formulas, while the produced wastes (bags) were stored and disposed together.

Mixing: The raw materials and the auxiliary materials were fed into a mixer to mix well. This step is a key control point that the mixing time must be strictly controlled by regular inspection of mixing uniformity. The mixer was equipped with a pulse dust collector to remove dust.

Pelletizing: The products obtained from mixing the raw materials and the auxiliary materials were introduced into a pelletizing machine with a 1.3% hydroxypropyl methyl cellulose aqueous solution according to a mass ratio of 100:35. The pelletizing machine was then started up to operate mixing and cutter for 3-5 minutes. After pelletizing was complete, the materials were dried in a fluidized bed for 30 minutes and then sieved by 16-mesh sieve.

Packaging and inspection: The products were weighed and packaged according to packaging specifications, stored in finished-product warehouses, and labeled with production and inspection information. At least two samples were collected for each batch and sent to the testing laboratory for inspection and as reserve samples. The products would be allowed to leave the factory only after passing the inspection. Thereby the hybrid pellet feed additive was obtained.

Cleaning production equipment: After production of each batch was complete, the production area must be cleaned. When changing the product, the production equipment shall be cleaned to remove impurities in order to prevent cross-contamination.

III. Animal Breeding Experiment

Embodiment A: Application Effect of Conjugate Acid Salts of N,N-Dimethylglycine with Metal and Organic Acid in Broiler Feed The experiment was carried out by single-factor randomized design. 1080 22-day-old Sanhuang broilers having similar body weight (averagely 153 g) were collected and randomly divided into 9 groups, 6 replicates in each group, 20 broilers in each replicate, with equal numbers of males and females. The henhouse and utensils were disinfected before the experiment. The broilers were kept in cages in the same henhouse under the same breeding conditions during the experiment. The basic diets mainly composed of corn and soybean meal, and no other antioxidant ingredients and growth promoters were added during the whole breeding process. The groups included a blank group, a control group, and experiment groups 1-7. The blank group was provided with only the basic diets, while the control group and the test groups 1-7 were respectively provided with 5000 ppm of the hybrid pellet feed additive products (see the "Preparation method of feed composition" section) in the basic diets. The experiment was carried out for 20 days, wherein the test broilers were fed with food and water ad libitum, and the ration were provided twice a day. For each replicate, the broilers were weighed (stopped feeding for 12 hours while water supply was maintained) at 42-day-old and their feed consumptions were recorded so as to calculate the average daily feed intake (ADFI), average daily weight gain (ADG) and feed conversion ratio (FCR). The experiment data were analyzed with SPSS18 software. The data were first analyzed by single factor analysis of variance (ANOVA), and if the differences between the groups were significant, multiple comparisons were performed using Duncan's method wherein the significance level was 0.05. Test results are expressed as "mean value±standard error" as shown in Table 4. As can be seen from the results, compared with the blank group, the control group and the experiment groups showed no significant effect on the feed intake of the test broilers, but a significant increase in the average daily weight gains and a significant reduction in the feed conversion ratio. Compared with the control group, the experiment groups showed no significant change in the average daily weight gain of the broilers, the test groups 1-3 showed no significant reduction in the feed conversion ratio, and the test groups 4-7 showed a significant reduction in the feed conversion ratio.

Conclusion: In the breeding experiment of broilers, with respect to feed conversion efficiency, the conjugate acid salt of calcium N,N-dimethylglycinate with benzoic acid, conjugate acid salt of calcium N,N-dimethylglycinate with fumaric acid, and conjugate acid salt of calcium N,N-dimethylglycinate with tetradecanoic acid provided by the present invention showed a breeding effect equivalent to that of sodium N,N-dimethylglycinate, while the conjugate acid salt of copper N,N-dimethylglycinate with benzoic acid, conjugate acid salt of zinc N,N-dimethylglycinate with benzoic acid, conjugate acid salt of copper N,N-dimethylglycinate with fumaric acid, and conjugate acid salt of zinc N,N-dimethylglycinate with fumaric acid provided by the present invention showed a breeding effect higher than that of sodium N,N-dimethylglycinate, giving a 10%-11.5% reduction in the feed conversion ratio as compared with the group which was not provided with any feed additives.

TABLE 4

Effect of conjugate acid salts of N,N-dimethylglycine with metal and organic acid on the production performance of broilers

|  | Sample | Amount | ADFI (g) | ADG (g) | FCR |
|---|---|---|---|---|---|
| Blank | — | 20*6 | 651.33 ± 15.00 | 216.00 ± 4.33$^a$ | 3.02 ± 0.02$^a$ |
| Control | Reference 1 | 20*6 | 703.00 ± 15.92 | 246.89 ± 8.38$^b$ | 2.85 ± 0.04$^b$ |
| Experiment 1 | Product 1 | 20*6 | 679.50 ± 15.46 | 245.87 ± 7.89$^b$ | 2.77 ± 0.04$^{bc}$ |
| Experiment 2 | Product 2 | 20*6 | 680.67 ± 12.87 | 246.27 ± 2.21$^b$ | 2.76 ± 0.04$^{bc}$ |
| Experiment 3 | Product 3 | 20*6 | 674.33 ± 13.83 | 237.53 ± 7.26$^b$ | 2.84 ± 0.03$^b$ |
| Experiment 4 | Product 4 | 20*6 | 662.00 ± 14.07 | 248.85 ± 8.62$^b$ | 2.67 ± 0.04$^{cd}$ |
| Experiment 5 | Product 5 | 20*6 | 674.17 ± 4.72 | 248.05 ± 3.74$^b$ | 2.72 ± 0.04$^{cd}$ |
| Experiment 6 | Product 6 | 20*6 | 655.17 ± 12.26 | 246.73 ± 2.59$^b$ | 2.67 ± 0.04$^d$ |
| Experiment 7 | Product 7 | 20*6 | 658.83 ± 10.51 | 242.91 ± 1.74$^b$ | 2.71 ± 0.04$^{cd}$ |

Note:
Data listed in the same column but labelled with different letters indicates there is a significant difference therebetween (P < 0.05); this rule is also applied hereinafter.

Embodiment B: Application Effect of Conjugate Acid Salts of N,N-Dimethylglycine with Metal and Organic Acid in Pig Feed Two hundred and forty (240) 65-day-old lean Duroc×Landrace×Large White pigs having similar body weight were randomly divided into 8 groups, 3 replicates in each group, 10 pigs in each replicate, with equal numbers of males and females. The pigsty and utensils were disinfected before the experiment. The pigs were kept in pens in the same pigsty under the same breeding conditions during the experiment. During the experiment, the experiment pigs were fed with food and water ad libitum, and the diet were provided twice a day. The groups included a control group and experiment groups 1-7. The control group was provided with only the basic diet, while the experiment groups 1-7 were respectively provided with the basic diets together with 1150 ppm of the hybrid pellet feed additive products 1-7 provided by the present invention. No other antioxidant ingredients and growth promoters were added during the whole breeding process. The experiment was carried out for 28 days. For each replicate, production performance of the pigs was measured, including the average daily feed intake (ADFI), average daily weight gain (ADG) and feed conversion ratio (FCR). The experiment data were analyzed with SPSS18 software. The data were first analyzed by single factor analysis of variance (ANOVA), and if the differences between the groups were significant, multiple comparisons were performed using Duncan's method wherein the significance level was 0.05. Test results are expressed as "mean value±standard error" as shown in Table 5. As can be seen from the results, compared with the control group, the experiment groups, which were provided with the conjugate acid salts of N,N-dimethylglycine with metal and organic acid, showed no significant effect on the feed intake of the pigs but a significant increase in the average daily weight gains and a reduction of 6.8%-12.2% in the feed conversion ratio. In addition, conjugate acid salts of copper N,N-dimethylglycinate with organic acid and conjugate acid salts of zinc N,N-dimethylglycinate with organic acid showed an improvement effect on the production performance of pigs better than that of conjugate acid salts of calcium N,N-dimethylglycinate with organic acid.

TABLE 5

Effect of conjugate acid salts of N,N-dimethylglycine with metal and organic acid on the production performance of pigs

|  | Sample | Amount | ADFI (kg) | ADG (kg) | FCR |
|---|---|---|---|---|---|
| Control |  | 10*3 | 11.87 ± 0.32 | 4.51 ± 0.08$^a$ | 2.63 ± 0.02$^a$ |
| Experiment 1 | Product 1 | 10*3 | 12.73 ± 0.33 | 5.24 ± 0.10$^b$ | 2.43 ± 0.02$^b$ |
| Experiment 2 | Product 2 | 10*3 | 12.40 ± 0.26 | 5.11 ± 0.07$^b$ | 2.43 ± 0.02$^b$ |
| Experiment 3 | Product 3 | 10*3 | 12.77 ± 0.20 | 5.20 ± 0.10$^b$ | 2.45 ± 0.01$^b$ |
| Experiment 4 | Product 4 | 10*3 | 12.53 ± 0.27 | 5.42 ± 0.12$^b$ | 2.31 ± 0.01$^c$ |
| Experiment 5 | Product 5 | 10*3 | 12.70 ± 0.26 | 5.47 ± 0.13$^b$ | 2.32 ± 0.01$^{cd}$ |
| Experiment 6 | Product 6 | 10*3 | 12.43 ± 0.43 | 5.24 ± 0.21$^b$ | 2.38 ± 0.01$^e$ |
| Experiment 7 | Product 7 | 10*3 | 12.50 ± 0.38 | 5.28 ± 0.18$^b$ | 2.37 ± 0.01$^{de}$ |

Embodiment C: Application Effect of Conjugate Acid Salts of N,N-Dimethylglycine with Metal and Organic Acid in Aquatic Feed (1) Experiment Materials Test fish: The experiment fish were grass carps, born at the year of the test, from Dafeng hatchery in Huizhou City, Guangdong Province. Healthy and lively grass carps of the same size were reared in big net cages (4×2×1.5 m$^3$) for four weeks before the breeding experiment. The experiment system included floating small net cages (1.1×1.1×1.1 m$^3$), each small net cage was provided with an aerator and aerated 24 hours every day. The small net cages were disposed together with temporary-rearing net cages in a 3500 m$^2$ pond in the test area, the pond had a depth of 1.55 m and the water in the pond was fully aerated groundwater. 384 fish which were similar in body weight and had been starved for 1 day were randomly divided into 8 groups, 4 replicates in each group and 12 fish in each replicate. The fish of each replicate were weighed and transferred to 36 net cages, and fed with different test feeds respectively.

Experiment feeds: The experiment feeds were prepared according to Table 6. The groups were respectively provided with different conjugate acid salts of N,N-dimethylglycine with metal and organic acid in the same concentration according to Table 7. Raw materials of the feed were ultra-pulverized, and then turned into floating expanded feed having a particle size of 3 mm by using a feed extruder from Jiangsu Muyang Group Co., Ltd. wherein the extruding temperature was 130° C., and 3% of soybean oil was sprayed on the feed using an oil sprayer. The feed was then sealed and stored in a cool place for later use.

TABLE 6

Formula and chemical composition of the experiment feed for grass carp (% wt.)

| Raw material | Content (%) | Raw material | Content (%) |
|---|---|---|---|
| Fish meal | 9.0 | Soybean oil | 3.0 |
| Intestine submucosa powder | 3.0 | Phospholipid rapeseed meal | 9.0 |
| Soybean meal | 12.0 | Gluten flour | 4.0 |
| Rapeseed meal | 12.0 | Blood cell powder | 2.0 |
| MSG protin | 3.0 | Vc-phosphate ester | 0.1 |
| Wheat middling | 12.6 | Monocalcium phosphate | 1.8 |
| Flour | 17.0 | Choline chloride | 0.2 |
| Bentonite | 0.70 | Multi-vitamin | 0.1 |
| Rice bran | 10.0 | Trace mineral element premix | 0.5 |

TABLE 7

Grouping of growth promotion experiment of conjugate acid salts of N,N-dimethylglycine with metal and organic acid

| Group | Sample | Concentration (ppm) |
|---|---|---|
| Blank control | — | — |
| Experiment 1 | Conjugate acid salt of calcium N,N-dimethylglycinate with benzoic acid | 450 |
| Experiment 2 | Conjugate acid salt of calcium N,N-dimethylglycinate with fumaric acid | 450 |

TABLE 7-continued

Grouping of growth promotion experiment of conjugate acid salts of N,N-dimethylglycine with metal and organic acid

| Group | Sample | Concentration (ppm) |
|---|---|---|
| Experiment 3 | Conjugate acid salt of calcium N,N-dimethylglycinate with tetradecanoic acid | 450 |
| Experiment 4 | Conjugate acid salt of copper N,N-dimethylglycinate with benzoic acid | 450 |
| Experiment 5 | Conjugate acid salt of copper N,N-dimethylglycinate with fumaric acid | 450 |
| Experiment 6 | Conjugate acid salt of zinc N,N-dimethylglycinate with benzoic acid | 450 |
| Experiment 7 | Conjugate acid salt of zinc N,N-dimethylglycinate with fumaric acid | 450 |

(2) Experiment Method

Test management: The experiment was carried out with diet restriction, the diet amount was adjusted once a week, the feeding level (based on initial weight) of each group was exactly the same, and feeding was conducted twice every day (at 7:30 and 15:00). The experiment was carried out for 8 weeks. During the experiment, water quality was monitored regularly to maintain the following conditions: water temperature 26.88±3.08° C., DO>5.0 mg O L$^{-1}$, pH 7.8, ammonia nitrogen <0.50 mg N L$^{-1}$, and nitrite nitrogen <0.05 mg N L$^1$.

Parameter statistics: In the experiment, the fish in each net cage were weighed as a whole after starved for 1 day so as to calculate their weight gain (WG, %), feed conversion ratio (FCR) and survival rate (SR, %), through the following formula.

Weight gain (WG, %)=100×(average final weight−average initial weight)/average initial weight Feed conversion ratio (FCR)=feed intake/fish weight gain Survival rate (SR, %)=100×fish amount at the end of the test/fish amount at the beginning of the test (3) Experiment Results Effect of conjugate acid salts of N,N-dimethylglycine with metal and organic acid on the production performance of grass carps is as shown in Table 8. Results showed that, the groups provided with conjugate acid salts of N,N-dimethylglycine with metal and organic acid were better than the blank control group in terms of weight gain and feed conversion ratio, indicating obvious growth-promotion effects, and the survival rate of grass carps were also significantly improved, indicating an significant improvement of anoxic resistance of grass carps.

TABLE 8

Test results of application of conjugate acid salts of N,N-dimethylglycine with metal and organic acid in fish feed

| | Initial weight (g) | Final weight (g) | Weight gain (%) | (FCR) | SR (%) |
|---|---|---|---|---|---|
| Blank control | 251.25 ± 2.68 | 574.64 ± 11.04 | 133.15 ± 4.54 | 1.56 ± 0.04 | 55.31 ± 2.57$^a$ |
| Test 1 | 249.81 ± 4.09 | 586.87 ± 10.44 | 134.96 ± 2.82 | 1.48 ± 0.03 | 83.10 ± 3.65$^b$ |
| Test 2 | 246.56 ± 3.54 | 589.33 ± 12.75 | 138.98 ± 3.02 | 1.48 ± 0.03 | 83.90 ± 5.30$^b$ |
| Test 3 | 249.62 ± 2.51 | 585.22 ± 11.23 | 134.40 ± 2.90 | 1.46 ± 0.04 | 73.00 ± 3.63$^b$ |
| Test 4 | 246.81 ± 7.18 | 598.68 ± 9.66 | 143.40 ± 10.09 | 1.41 ± 0.03 | 80.04 ± 3.80$^b$ |
| Test 5 | 250.31 ± 6.28 | 598.12 ± 9.27 | 139.12 ± 2.34 | 1.43 ± 0.03 | 83.96 ± 5.68$^b$ |
| Test 6 | 256.75 ± 6.69 | 597.66 ± 9.69 | 133.08 ± 4.70 | 1.45 ± 0.03 | 78.04 ± 4.21$^b$ |
| Test 7 | 250.31 ± 7.05 | 600.00 ± 9.30 | 139.98 ± 3.58 | 1.44 ± 0.02 | 84.94 ± 4.26$^b$ |

Technical features of the embodiments described above can be arbitrarily combined. In order to simplify the description, all possible combinations of the technical features in the above embodiments have not been described; however, as long as there is no contradiction in these combinations of the technical features, they should be considered to fall under the scope described in this specification.

The above-mentioned embodiments only express several implementation manners of the present invention, with more specific and detailed description, but they cannot be understood as limiting the scope of the invention. It should be noted that, for those of ordinary skill in the art, without departing from the concept of the present invention, several modifications and improvements can be made, which all belong to the scope of the present invention. Therefore, the scope of the invention shall be determined by the appended claims.

What is claimed is:

1. A conjugate acid salt of N,N-dimethylglycine with a metal and an organic acid, wherein the conjugate acid salt has a following structural formula:

[(CH$_3$)$_2$NCH$_2$COO]$_n$M.[Organic acid]

wherein n is 1 or 2; M is selected from an alkali metal ion or a divalent metal ion; the organic acid is selected from an organic polyacid, a C$_2$-C$_{18}$ linear fatty acid or an aromatic acid.

2. The conjugate acid salt of N,N-dimethylglycine with the metal and the organic acid according to claim 1, wherein the organic polyacid is selected from fumaric acid, maleic acid, tartaric acid, succinic acid, malonic acid, malic acid, dihydroxypropionic acid, pyruvic acid, glycolic acid, gluconic acid, galactonic acid, aspartic acid, glutamic acid, citric acid or oxalic acid; the C$_2$-C$_{18}$ linear fatty acid is selected from acetic acid, propionic acid, butyric acid, capric acid, palmitic acid, lauric acid or stearic acid; and the aromatic acid is selected from benzoic acid, p-toluic acid, naphthoic acid, mandelic acid, p-chlorobenzoic acid, p-bromobenzoic acid, p-aminobenzoic acid, cinnamic acid, salicylic acid, acetylsalicylic acid, p-methylbenzenesulfonic acid or benzenesulfonic acid.

3. The conjugate acid salt of N,N-dimethylglycine with the metal and the organic acid according to claim 1, wherein the organic acid is benzoic acid, p-toluic acid or fumaric acid.

4. The conjugate acid salt of N,N-dimethylglycine with the metal and the organic acid according to claim 1, wherein the divalent metal ion is selected from Ca(II), Mg(II), Cu(II), Zn(II), Fe(II), Mn(II), Co(II) or Ni(II).

5. The conjugate acid salt of N,N-dimethylglycine with the metal and the organic acid according to claim 1, wherein the conjugate acid salt is selected from: $[(CH_3)_2NCH_2COO]_2$ Ca.[Benzoic acid], $[(CH_3)_2NCH_2COO]_2$Ca.[Fumaric acid], $[(CH_3)_2NCH_2COO]_2$Cu.[Benzoic acid], $[(CH_3)_2NCH_2COO]_2$Cu.[Fumaric acid], $[(CH_3)_2NCH_2COO]_2$Zn.[Benzoic acid], or $[(CH_3)_2NCH_2COO]_2$Zn.[Fumaric acid].

6. A method of preparing an animal feed additive comprising mixing the conjugate acid salt of N,N-dimethylglycine with the metal and the organic acid of claim 1 with a carrier acceptable in a pharmaceutical, a foodstuff or a feed.

7. A method of preparing an animal feed comprising mixing the conjugate acid salt of N,N-dimethylglycine with the metal and the organic acid of claim 1 with a carrier acceptable in a pharmaceutical, a foodstuff or a feed.

8. A feed composition comprising at least one of the conjugate acid salt of N,N-dimethylglycine with the metal and the organic acid of claim 1, and a carrier acceptable in a pharmaceutical, a foodstuff or a feed.

9. The feed composition according to claim 8, further comprising a nutritional feed additive and/or a non-nutritional feed additive.

10. The feed composition according to claim 8, further comprising a feed raw material.

11. A method of preparing an animal feed additive comprising mixing the conjugate acid salt of N,N-dimethylglycine with the metal and the organic acid of claim 5 with a carrier acceptable in a pharmaceutical, a foodstuff or a feed.

12. A method of preparing an animal feed comprising mixing the conjugate acid salt of N,N-dimethylglycine with the metal and the organic acid of claim 5 with a carrier acceptable in a pharmaceutical, a foodstuff or a feed.

13. A feed composition comprising at least one of the conjugate acid salt of N,N-dimethylglycine with the metal and the organic acid of claim 5, and a carrier acceptable in a pharmaceutical, a foodstuff or a feed.

14. The feed composition according to claim 13, further comprising a nutritional feed additive and/or a non-nutritional feed additive.

15. The feed composition according to claim 13, further comprising a feed raw material.

16. A method of preparing an animal feed additive comprising mixing the feed composition of claim 8 with a carrier acceptable in a pharmaceutical, a foodstuff or a feed additive.

17. A method of preparing an animal feed comprising mixing the feed composition of claim 8 with a carrier acceptable in a pharmaceutical, a foodstuff or a feed.

* * * * *